(12) United States Patent
Young

(10) Patent No.: US 8,961,617 B2
(45) Date of Patent: Feb. 24, 2015

(54) AMNION AND CHORION CONSTRUCTS AND USES THEREOF IN ABDOMINAL SURGERY

(71) Applicant: AFcell Medical, Parsippany, NJ (US)

(72) Inventor: Robin R. Young, Wayne, PA (US)

(73) Assignee: Liventa Bioscience, Inc., West Conshohocken, PA (US)

(*) Notice: Subject to any disclaimer, the term of this patent is extended or adjusted under 35 U.S.C. 154(b) by 0 days.

(21) Appl. No.: 13/790,703

(22) Filed: Mar. 8, 2013

(65) Prior Publication Data

US 2013/0238100 A1 Sep. 12, 2013

Related U.S. Application Data

(60) Provisional application No. 61/608,395, filed on Mar. 8, 2012.

(51) Int. Cl.
| | | |
|---|---|---|
| *A61F 2/02* | (2006.01) | |
| *A61L 27/36* | (2006.01) | |
| *A61F 2/00* | (2006.01) | |
| *A61F 2/04* | (2013.01) | |

(52) U.S. Cl.
CPC ............ *A61F 2/02* (2013.01); *A61L 27/3604* (2013.01); *A61F 2/0063* (2013.01); *A61F 2002/045* (2013.01); *A61F 2230/0008* (2013.01); *A61F 2230/0019* (2013.01); *A61F 2230/0023* (2013.01); *A61F 2230/0065* (2013.01)
USPC ...................................... 623/23.72

(58) Field of Classification Search
USPC ............ 623/13.17–13.18, 14.13, 16.1, 15.12, 623/23.64–23.76; 424/93.7, 422, 423, 426, 424/572; 128/898
See application file for complete search history.

(56) References Cited

U.S. PATENT DOCUMENTS

| | | |
|---|---|---|
| 1,699,479 A | 1/1929 | Scott |
| 4,400,833 A | 8/1983 | Kurland |
| 4,585,458 A | 4/1986 | Kurland |
| 5,480,424 A | 1/1996 | Cox |
| 5,612,028 A | 3/1997 | Sackier et al. |

(Continued)

FOREIGN PATENT DOCUMENTS

| | | |
|---|---|---|
| DE | 19513177 A1 | 10/1996 |
| WO | 0073421 A2 | 12/2000 |

(Continued)

OTHER PUBLICATIONS

Yang et al, "New skin-equivalent model from de-epithelialized amnion membrane", Cell Tissue Research, vol. 326, pp. 69-77 (2006).

(Continued)

*Primary Examiner* — Suzette J Gherbi
(74) *Attorney, Agent, or Firm* — Panitch Schwarze Belisario & Nadel LLP

(57) ABSTRACT

A construct for use in an abdominal surgery is described. The construct contains an allograft having at least one layer of human amnion and chorion tissues, and has a size and shape appropriate for covering an incision or a surgical site resulting from the surgery. Methods of preparing the construct and using it in an abdominal surgery are also described. The products and methods improve the performance of the abdominal surgery, e.g., by reducing adhesions, scar formation while also reducing inflammation and risk of post-operative infection.

15 Claims, 4 Drawing Sheets

(56) References Cited

U.S. PATENT DOCUMENTS

| | | | |
|---|---|---|---|
| 6,087,552 A * | 7/2000 | Gregory | 623/1.41 |
| 6,152,142 A | 11/2000 | Tseng | |
| 6,326,019 B1 | 12/2001 | Tseng | |
| 6,734,018 B2 | 5/2004 | Wolfinbarger, Jr. et al. | |
| 6,740,122 B1 * | 5/2004 | Pajotin | 606/151 |
| 6,872,384 B1 | 3/2005 | Franklin et al. | |
| 7,160,333 B2 | 1/2007 | Plouhar et al. | |
| 7,244,444 B2 | 7/2007 | Bates | |
| 7,255,879 B2 | 8/2007 | Hariri | |
| 8,105,634 B2 | 1/2012 | Liu et al. | |
| 8,129,359 B2 | 3/2012 | Herzberg et al. | |
| 8,323,701 B2 | 12/2012 | Daniel et al. | |
| 2001/0003986 A1 | 6/2001 | Cosgrove | |
| 2001/0050083 A1 | 12/2001 | Marchitto et al. | |
| 2001/0053839 A1 | 12/2001 | Noishiki et al. | |
| 2002/0026092 A1 | 2/2002 | Buckberg et al. | |
| 2003/0023316 A1 | 1/2003 | Brown et al. | |
| 2003/0187515 A1 | 10/2003 | Hariri et al. | |
| 2003/0212456 A1 | 11/2003 | Lipchitz et al. | |
| 2004/0048796 A1 | 3/2004 | Hariri et al. | |
| 2004/0181240 A1 | 9/2004 | Tseng et al. | |
| 2005/0113938 A1 | 5/2005 | Jamiolkowski et al. | |
| 2005/0137704 A1 | 6/2005 | Steenlage | |
| 2005/0186193 A1 | 8/2005 | Mishra | |
| 2005/0214259 A1 | 9/2005 | Sano et al. | |
| 2006/0153928 A1 | 7/2006 | Kinoshita et al. | |
| 2007/0021762 A1 | 1/2007 | Liu et al. | |
| 2007/0061013 A1 | 3/2007 | Cauthen, III et al. | |
| 2007/0191849 A1 | 8/2007 | ElAttrache et al. | |
| 2007/0198059 A1 | 8/2007 | Patel et al. | |
| 2007/0233135 A1 | 10/2007 | Gil et al. | |
| 2007/0270953 A1 | 11/2007 | Trieu | |
| 2008/0027477 A1 | 1/2008 | Obermiller et al. | |
| 2008/0046095 A1 | 2/2008 | Daniel | |
| 2008/0188766 A1 | 8/2008 | Gertner | |
| 2008/0193554 A1 | 8/2008 | Dua et al. | |
| 2008/0269899 A1 | 10/2008 | Horton | |
| 2008/0274184 A1 | 11/2008 | Hunt | |
| 2009/0125119 A1 | 5/2009 | Obermiller et al. | |
| 2009/0142396 A1 | 6/2009 | Odar et al. | |
| 2009/0204228 A1 | 8/2009 | Hiles | |
| 2010/0080779 A1 | 4/2010 | Smith et al. | |
| 2010/0104539 A1 * | 4/2010 | Daniel et al. | 424/93.7 |
| 2010/0106178 A1 | 4/2010 | Obermiller et al. | |
| 2010/0161345 A1 | 6/2010 | Cain et al. | |
| 2010/0228335 A1 | 9/2010 | Schorgl et al. | |
| 2010/0324693 A1 | 12/2010 | Hardenbrook | |
| 2011/0152898 A1 | 6/2011 | Kochevar et al. | |
| 2011/0256202 A1 | 10/2011 | Tom et al. | |
| 2011/0274666 A1 * | 11/2011 | Turner et al. | 424/93.7 |
| 2011/0307059 A1 | 12/2011 | Young et al. | |
| 2011/0319989 A1 | 12/2011 | Lane et al. | |
| 2012/0010708 A1 | 1/2012 | Young et al. | |
| 2012/0010727 A1 | 1/2012 | Young et al. | |
| 2012/0020933 A1 | 1/2012 | Young et al. | |
| 2012/0035743 A1 | 2/2012 | Young et al. | |
| 2012/0035744 A1 | 2/2012 | Young et al. | |
| 2012/0078378 A1 | 3/2012 | Daniel et al. | |
| 2012/0083900 A1 | 4/2012 | Samaniego et al. | |
| 2012/0141595 A1 | 6/2012 | Tseng et al. | |
| 2012/0179176 A1 | 7/2012 | Wilson et al. | |
| 2012/0251526 A1 | 10/2012 | Smith et al. | |
| 2012/0269880 A1 | 10/2012 | Tseng et al. | |
| 2012/0294910 A1 | 11/2012 | Daniel et al. | |
| 2012/0301444 A1 * | 11/2012 | Clarke et al. | 424/93.7 |
| 2013/0156863 A1 | 6/2013 | Tseng et al. | |
| 2013/0209524 A1 | 8/2013 | Young | |
| 2013/0211503 A1 | 8/2013 | Young | |
| 2013/0211504 A1 | 8/2013 | Young | |
| 2013/0211511 A1 | 8/2013 | Young | |
| 2013/0237747 A1 * | 9/2013 | Linares et al. | 600/37 |
| 2013/0344163 A1 | 12/2013 | Tseng et al. | |
| 2014/0037598 A1 | 2/2014 | Jansen et al. | |
| 2014/0052274 A1 | 2/2014 | Koob et al. | |
| 2014/0141152 A1 * | 5/2014 | Sostek et al. | 427/2.24 |
| 2014/0147511 A1 | 5/2014 | Tseng et al. | |
| 2014/0171969 A1 * | 6/2014 | Kraemer et al. | 606/142 |

FOREIGN PATENT DOCUMENTS

| | | |
|---|---|---|
| WO | 2009044408 A1 | 4/2009 |
| WO | 2009132186 A1 | 10/2009 |

OTHER PUBLICATIONS

Office Action issued Dec. 31, 2012 in U.S. Appl. No. 13/177,177.
U.S. Appl. No. 13/767,204 by Young, filed Feb. 14, 2013.
U.S. Appl. No. 13/767,210 by Young, filed Feb. 14, 2013.
U.S. Appl. No. 13/767,215 by Young, filed Feb. 14, 2013.
U.S. Appl. No. 13/767,221 by Young, filed Feb. 14, 2013.
U.S. Appl. No. 13/767,224 by Young, filed Feb. 14, 2013.
Office Action issued May 23, 2013 in U.S. Appl. No. 13/177,177.
U.S. Appl. No. 13/804,731 by Young, filed Mar. 14, 2013.
U.S. Appl. No. 13/804,785 by Young, filed Mar. 14, 2013.
U.S. Appl. No. 13/790,712 by Young, filed Mar. 8, 2013.
Office Action issued Jun. 10, 2013 in U.S. Appl. No. 13/179,966.
Ozgenel et al, "Effects of human amniotic fluid on peripheral nerve scarring and regeneration in rats," Journal of Neurosurgery, vol. 98, pp. 371-377 (2003).
Office Action issued Jul. 15, 2013 in U.S. Appl. No. 13/195,189 by Young.
Office Action issued Nov. 15, 2013 in U.S. Appl. No. 13/179,966.
Office Action issued Nov. 21, 2013 in U.S. Appl. No. 13/178,980.
Khalid et al, "Suturing of lacerations of skeletal muscle," J. Hand Microsurg., vol. 1, No. 1, pp. 54-59 (Jun. 2009).
Kragh et al, "Suturing of lacerations of skeletal muscle," The Journal of Bone and Joint Surgery, vol. 87, No. 9, pp. 1303-1305 (Sep. 2005).
Office Action issued Nov. 27, 2013 in U.S. Appl. No. 13/177,177.
Office Action issued Nov. 29, 2013 in U.S. Appl. No. 13/195,189.
Office Action issued Dec. 20, 2013 in U.S. Appl. No. 13/767,221.
Novitzky et al, "The Transplantation and Replacement of Thoracic Organs," Chapter 11, pp. 81-87 (1990).
Jabareen et al, "Relation between mechanical properties and microstructure of human fetal membranes: An attempt towards a quantitative analysis," Eur. J. of Ob. Gyn. Reprod. Biol., vol. 144S, pp. 5134-5141 (2009).
Maisch et al, "Guideline on the Diagnosis and Management of Pericardial Diseases," Eur. Heart J., pp. 1-28 (2004).
Office Action issued Jan. 31, 2014 in U.S. Appl. No. 13/157,643 by Young.
Office Action issued Feb. 12, 2014 in U.S. Appl. No. 13/198,330 by Young.
Office Action issued Jul. 3, 2014 in U.S. Appl. No. 13/198,330.
Office Action issued Jul. 15, 2014 in U.S. Appl. No. 13/767,215.
Sorsby et al, "Further Experience with Amniotic Membrane Grafts in Caustic Burns of the Eye", British Journal of Ophthalmology, vol. 31, No. 7, pp. 409-418 (1947).
Kim et al, "Transplantation of Preserved Human Amniotic Membrane for Surface Reconstruction in Severely Damaged Rabbit Corneas", Cornea, vol. 14, No. 5, pp. 473-484 (1995).
Kruse et al, "Cryopreserved human amniotic membrane for ocular surface reconstruction", Graefe's Archive for Clinical and Experimental Ophthalmology, vol. 238, pp. 68-75 (2000).
Solomon et al, "Suppression of interleuken 1alpha and interleukin 1beta in human limbal epithelial cells cultured on the amniotic membrane stromal matrix", British Journal of Ophthalmology, vol. 85, No. 4, pp. 444-449 (2001).
Hao et al, "Identification of Antiangiogenic and Antiinflammatory Proteins in Human Amniotic Membrane", Cornea, vol. 19, No. 3, pp. 348-352 (2000).
Kim et al, "Amniotic Membrane Patching Promotes Healing and Inhibits Proteinase Activity on Wound Healing Following Acute Corneal Alkali Burn", Experimental Eye Research, vol. 70, No. 3, pp. 329-337 (2000).
Dua, "Perspective—Amniotic Membrane Transplantation", The British Journal of Ophthalmology, vol. 83, No. 6, pp. 748-752 (1999).

(56) References Cited

OTHER PUBLICATIONS

Tsai et al, "Human Allograft Limbal Transplantation for Corneal Surface Reconstruction", Cornea, vol. 13, No. 5, pp. 389-400 (1994).
Chao et al, "A New Method of preventing Adhesions. The Use of Amnioplastin after Craniotomy", The British Medical Journal, vol. 517, No. 1 (1940).
Trelford et al, American Journal of Obstetrics & Gynecology, vol. 134, pp. 833-845 (1979).
King et al, "Elafin in Human Endometrium: An Antiprotease and Antimicrobial Molecule Expressed during Menstruation", The Journal of Clinical Endocrinology & Metabolism, vol. 88, pp. 4426-4431 (2003).
Buhimschi et al, "The novel antimicrobial peptide beta3-defensin is produced by the amnion: A possible role of the fetal membranes in innate immunity of the amniotic cavity", American Journal of Obstetrics & Gynecology, vol. 191, pp. 1678-1687 (2004).
Krisanaprakornkit et al, "Expression of the Peptide Antibiotic Human beta-Defensin 1 in Cultured Gingival Epithelial Cells and Gingival Tissue", Infection and Immunity, vol. 66, pp. 4222-4228 (1998).
Harder et al, "Mucoid *Pseudomonas aeruginosa*, TNF-alpha, and IL-1 beta, but not IL-6, Induce Human beta-Defensin-2 in Respiratory Epithelia", American Journal of Respiratory Cell and Molecular Biology, vol. 22, pp. 714-721 (2000).
King et al, "Expression of Natural Antimicrobials by Human Placenta and Fetal Membranes", Placenta, vol. 28, No. 2, pp. 161-169 (2007).
Lee et al, "Suppression of TGF-beta signaling in both normal conjunctival fibroblasts and pterygial body fibroblasts by amniotic membrane", vol. 20, No. 4, pp. 325-334 (2000).
Tseng et al, "Suppression of transforming growth factor-beta isoforms, TGF-beta receptor type II, and myofibroblast differentiation in cultured human corneal and limbal fibroblasts by amniotic membrane matrix", vol. 179, No. 3, pp. 325-335 (1999).
Niknejad et al, "Properties of the amniotic membrane for potential use in tissue engineering", European Cells and Materials Journal, vol. 15, pp. 88-99 (2008).
Demirkan et al, "The use of amniotic membrane in flexor tendon repair: an experimental model", Archives of Orthopaedic and Trauma Surgery, vol. 122, No. 7, pp. 396-399 (2002).
Peacock, "Wound Repair", 3rd Ed., Wb Saunders & Co., pp. 263-331 (1984).
King et al, "Innate immune defences in the human endometrium", Reproductive Biology and Endocrinology, vol. 1, No. 116, pp. 1-8 (2003).
Burman et al, "Ophthalmic applications of preserved human amniotic membrane: A review of current indications", Cell and Tissue Banking, vol. 5, pp. 161-175 (2004).
Barabino et al, "Role of Amniotic Membrane Transplantation for Conjunctival Reconstruction in Ocular-Cicatricial Pemphigoid", Ophthalmology, vol. 110, No. 3, pp. 474-480 (Mar. 2003).
Kobayashi et al, "Multi-layer Amniotic Membrane Graft for Pterygium in a Patient with Xeroderma Pigmentosum", Japanese Journal of Opthalmology, vol. 45, pp. 496-498 (2001).
Hanada et al, "Multilayered Amniotic Memrane Transplantation for Severe Ulceration of the Cornea and Sclera", American Journal of Ophthalmology, vol. 131, No. 3, pp. 324-331 (Mar. 2001).
Meller et al, "Conjunctival Epithelial Cell Differentiation on Amniotic Membrane", Investigative Ophthalmology & Visual Science, vol. 40, No. 5, pp. 878-886 (Apr. 1999).
Rinastiti et al, "Histological evaluation of rabbit gingival wound healing transplanted with human amniotic membrane", International Journal of Oral & Maxillofacial Surgery, vol. 35, pp. 247-251 (2006).
Schwab, "Cultured corneal epithelia for ocular surface disease", Transactions of the American Ophthalmological Society, No. 135, pp. 891-986 (1999).
U.S. Appl. No. 14/290,391 by Young, filed May 29, 2014.
Office Action issued Apr. 17, 2014 in U.S. Appl. No. 13/178,980.
Office Action issued May 28, 2014 in U.S. Appl. No. 13/767,210.
Office Action issued Dec. 23, 2014 in U.S. Appl. No. 13/767,215.
Office Action issued Dec. 24, 2014 in U.S. Appl. No. 13/804,731.
Gepfert et al., Further Studies of the Intraperitoneal Use of Bovine Amniotic Fluid in Abdominal Surgery, Jan. 1939, The American Journal of Surgery, vol. 43, Issue 1, pp. 81-85.
Office Action issued Dec. 5, 2014 in U.S. Appl. No. 13/790,712.
Office Action issued Sep. 8, 2014 in U.S. Appl. No. 13/767,210.
Office Action issued Oct. 8, 2014 in U.S. Appl. No. 13/767,221.
Rahman (Rahman, I., et al., Amniotic membrane in ophthalmology: indications and limitations, Eye 23 (2009) pp. 1954-1961).

* cited by examiner

AMNION AND CHORION CONSTRUCTS AND USES THEREOF IN ABDOMINAL SURGERY

CROSS-REFERENCE TO RELATED APPLICATIONS

This application is entitled to priority pursuant to 35 U.S.C. §119(e) to U.S. Provisional Patent Application No. 61/608,395, filed Mar. 8, 2012, which is hereby incorporated by reference herein in its entirety.

BACKGROUND OF THE INVENTION

1. Field of Invention

Embodiments of the present invention relate to methods and products for improving abdominal surgery. In particular, embodiments of the present invention relate to constructs comprising an allograft having at least one layer of amnion and chorion tissues for use during abdominal surgeries. The constructs are adapted for the ease of use for covering the surgical site or incisions resulting from the surgery.

2. Background of the Invention

Abdominal surgery has been used broadly for the treatment or diagnosis of diseases affecting the abdominal cavity. The surgery involves opening a region in the abdomen. Complications of abdominal surgery include, but are not limited to, bleeding, infections or inflammations (such as, chest infections, intra-abdominal infection (peritonitis), wound infection, and other infections or inflammations), post-operative paralysis of the intestine (ileus), post-operative intestinal obstruction, urinary difficulties, adhesions, hernia formation, etc. For example, string-like adhesions may occur inside the abdominal cavity, leading to blockages of the bowel, sometimes after an abdominal surgery. Additional operations are sometimes necessary to divide or remove these adhesions or to unblock the bowel.

The amnion is a thin, cellular, extraembryonic membrane that forms the inner membrane of a closed placental sac surrounding and protecting an embryo in reptiles, birds, and mammals. The sac contains the fetus and amniotic fluid or liquor amnii, in which the embryo is immersed, nourished and protected. Amnion is a tough, transparent, nerve-free, and nonvascular membrane consisting of two layers of cells: an inner, single-cell-thick layer of ectodermal epithelium and an outer covering of mesodermal, connective, and specialized smooth muscular tissue. In the later stages of pregnancy, the amnion expands to come in contact with the inner wall of the chorion creating the appearance of a thin wall of the sac extending from the margin of the placenta. The amnion and chorion are closely applied, though not fused, to one another and to the wall of the uterus. Thus, at the later stage of gestation, the fetal membranes are composed of two principal layers: the outer chorion that is in contact with maternal cells and the inner amnion that is bathed by amniotic fluid.

The amnion has multiple functions, e.g., as a covering epithelium, as an active secretary epithelium, and for intense intercellular and transcellular transport. Before or during labor, the sac breaks and the fluid drains out. Typically, the remnants of the sac membranes are observed as the white fringe lining the inner cavity of the placenta expelled after birth. The amnion can be stripped off from the placenta. The amnion has a basement membrane side and a stroma side.

The fetal membrane including amnion and chorion has been used in surgeries documented as early as 1910. See Trelford et al., 1979, *Am J Obstet Gynecol*, 134:833-845. Amnioplastin, an isolated and chemically processed amniotic membrane, was used for continual dural repair, peripheral nerve injuries, conjunctival graft and flexor and muscle repair. See e.g., Chao et al., 1940, *The British Medical Journal*, March 30. The amnion has been used for multiple medical purposes, e.g., as a graft in surgical reconstruction forming artificial vaginas or over the surgical defect of total glossectomy, as a dressing for burns, on full-thickness skin wounds or in omphalocele, and in the prevention of meningocerebral adhesions following head injury or tissue adhesion in abdominal and pelvic surgery.

In recent years, there have been renewed interests in the application of amnion in ocular surface reconstruction, for example, as an allograph for repairing corneal defects. See, for example, Tsai and Tseng, *Cornea*. 1994 September; 13(5):389-400; and Dua et al., *Br. J. Ophthalmol* 1999, 83:748-20 752. In addition, amnion and amniotic fluid have recently been used as sources of placental stem cells. See, e.g., U.S. Pat. No. 7,255,879 and WO 200073421.

Despite the clinical and published record regarding the safety and efficacy of amnion in broad surgical use, issues regarding reproducibility, safety and the precise form of amnion for each prospective indication have prevented amnion from achieving broad commercial distribution.

There is a need of improved methods and products for abdominal surgeries that would enhance wound healing, effectively reduce inflammation and inhibit fibroblast formation, scarring and adhesion formation. The present invention relates to such improved methods and products.

It is now discovered that using amnion in abdominal surgeries as described in the present invention significantly reduces inflammation and tissue adhesion, promotes uniform re-growth and epithelialization, prevents scar tissue formation, thus significantly improves performance and reduces complications of abdominal surgeries.

BRIEF SUMMARY OF THE INVENTION

In one general aspect, the present invention relates to a construct for use in an abdominal surgery. The construct comprises an allograft comprising at least one layer of human amnion and chorion tissues, wherein the construct has a size and shape appropriate for covering an incision or a surgical site resulting from the surgery.

In another general aspect, the present invention relates to a method of preparing a construct for use in an abdominal surgery. The method comprises drying an allograft comprising at least one layer of human amnion and chorion tissues over a frame, preferably a rigid or semi rigid frame, of a shape appropriate for covering an incision or a surgical site resulting from the surgery.

Another general aspect of the present invention relates to an improved abdominal surgery. The improvement comprises covering an incision or a surgical site resulting from the surgery with an allograft comprising at least one layer of human amnion and chorion tissues, wherein the construct has a size and shape appropriate for covering the incision or the surgical site.

According to other embodiments of the present invention, the improvement to an abdominal surgery further comprises applying an amniotic fluid to the incision or the surgical site to thereby cover the incision or the surgical site with the amniotic fluid, and the kit further comprises an amniotic fluid and instructions on how to use the amniotic fluid in the abdominal surgery.

Yet another general aspect of the present invention relates to a kit, which comprises:

(a) a plurality of constructs for use in an abdominal surgery according to embodiments of the present invention; and (b) instructions on covering the incision or the surgical site resulting from the surgery with the constructs, wherein at least two of the constructs are different in at least one of size and shape.

Preferably, the kit further comprises an amniotic fluid and instructions on applying the amniotic fluid to cover the incision or the surgical site during the surgery.

In a preferred embodiment of the present invention, the human amnion and chorion tissues and amniotic fluid are obtained by a process comprising:

(a) obtaining informed consent from pregnant females;
(b) conducting risk assessment on the consented pregnant females to select an amnion donor;
(c) procuring after birth placenta from the amnion donor; and
(d) obtaining amnion and chorion tissues from the placenta.

Other aspects, features and advantages of the invention will be apparent from the following disclosure, including the detailed description of the invention and its preferred embodiments and the appended claims.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
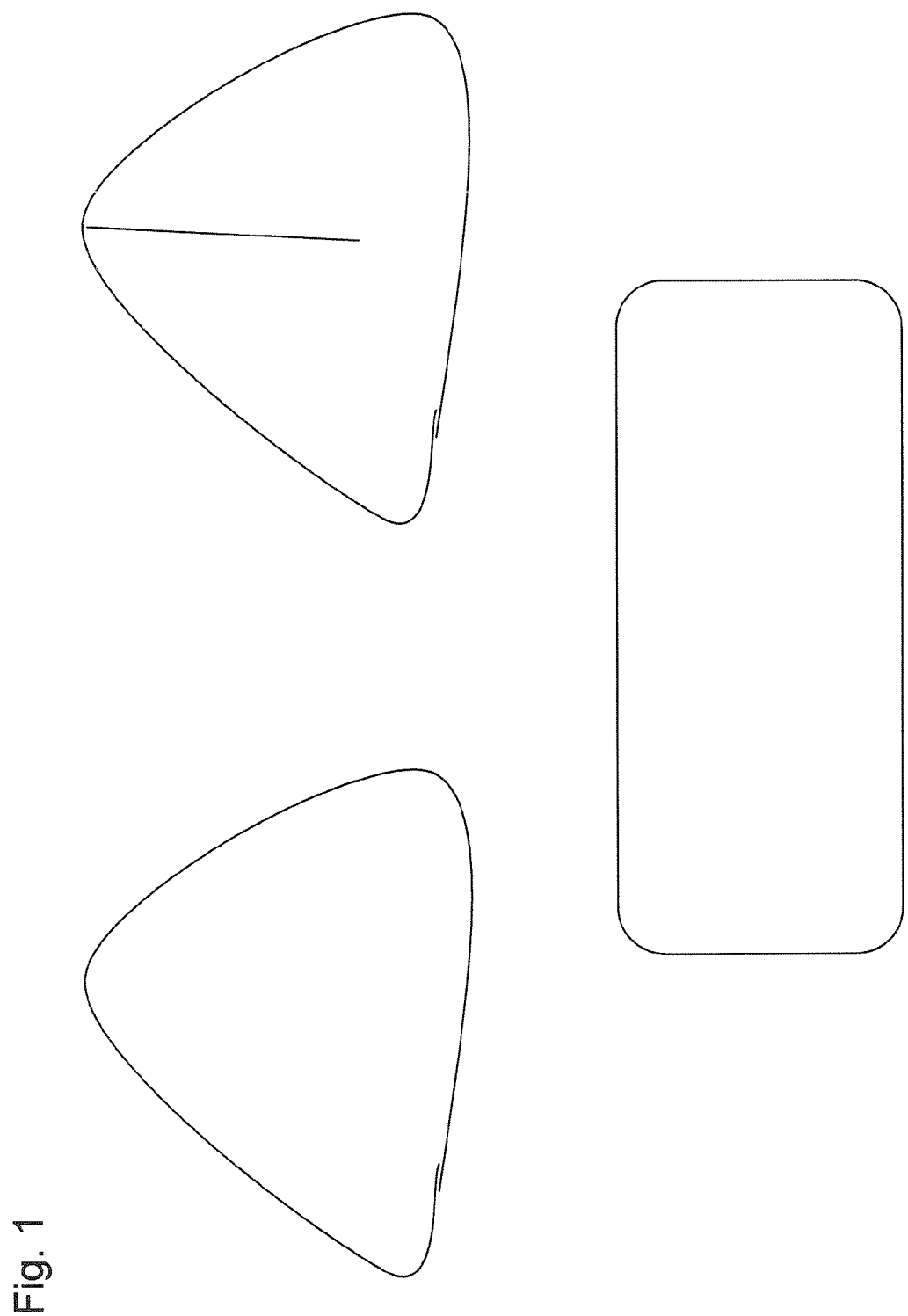
FIG. 1 illustrates constructs according to embodiments of the present invention that can be used in a liver resection, wherein all constructs have round corners, the generally triangle shaped constructs are equilateral triangles having a side of 3 cm, with or without a slit, which allows easy access of veins or vessels or going around raised structures, and the generally rectangle shaped construct has a dimension of 3 cm×4-10 cm.

Unless defined otherwise, all technical and scientific terms used herein have the same meaning as commonly understood to one of ordinary skill in the art to which this invention pertains. In this application, certain terms are used, which shall have the meanings as set in the specification. It must be noted that as used herein and in the appended claims, the singular forms "a," "an," and "the" include plural reference unless the context clearly dictates otherwise.

In one general aspect, the present invention relates to a construct for use in an abdominal surgery. The construct comprises an allograft comprising at least one layer of human amnion and chorion tissues, wherein the construct has a size and shape appropriate for covering an incision or a surgical site resulting from the surgery, thereby providing anti-adhesion, anti-microbial and anti-inflammatory functions to improve the surgery.

According to embodiments of the present invention, the allograft can be a single layer of amnion or chorion tissue, more than one layer of amnion or chorion tissue, or a combination of one or more layers of amnion tissue and one or more layers of chorion tissue. When the allograft is a combination of multiple layers of both amnion and chorion tissue, the layers can be arranged in any order. The multiple layers in the allograft can also be subject to a cross-linking treatment to make the layers closely adhere to each other in an integrated form.

Preferably, an allograft for covering a surgical site of an abdominal organ has a thickness about 0.02 mm to 0.10 mm.

Embodiments of the present invention can be used to improve the performance of any therapeutic or diagnostic procedure that involves the opening of an abdominal region. Examples of such procedures include, but are not limited to, abdomen specific procedures, such as exploratory laparotomy, reopening of recent laparotomy site, laparoscopy, biopsy of abdominal wall or umbilicus, biopsy of peritoneum, closed, percutaneous, or needle biopsy of intra-abdominal mass, peritoneal lavage, laparoscopic lysis of peritoneal adhesions, other lysis of peritoneal adhesions, suture of abdominal wall and peritoneum, reclosure of postoperative disruption of abdominal wall, delayed closure of granulating abdominal wound, other suture of abdominal wall, suture of peritoneum, repair of gastroschisis, other repair of abdominal wall, other repair of peritoneum, other repair of omentum, other repair of mesentery, percutaneous abdominal drainage, removal of foreign body from peritoneal cavity, creation of cutaneoperitoneal fistula, creation of peritoneovascular shunt, incision of peritoneum, injection of air into peritoneal cavity, injection of locally-acting therapeutic substance into peritoneal cavity, peritoneal dialysis, other operations of abdominal region.

The present invention can also be used in appendix specific procedures, such as laparoscopic appendectomy, other appendectomy, laparoscopic in appendectomy, other incidental appendectomy, appendicostomy, closure of appendiceal fistula, other operations on appendix.

The present invention can also be used in hernia procedures, such as laparoscopic repair of direct inguinal hernia with graft or prosthesis, laparoscopic repair of indirect inguinal hernia with graft or prosthesis, laparoscopic repair of inguinal hernia with graft or prosthesis, not otherwise specified, laparoscopic bilateral repair of direct inguinal hernia with graft or prosthesis, laparoscopic bilateral repair of indirect inguinal hernia with graft or prosthesis, laparoscopic bilateral repair of inguinal hernia, one direct and one indirect, with graft or prosthesis, laparoscopic bilateral repair of inguinal hernia with graft or prosthesis, not otherwise specified, laparoscopic robotic assisted procedure, unilateral repair of inguinal hernia, not otherwise specified, other and open repair of direct inguinal hernia, other and open repair of indirect inguinal hernia, other and open repair of direct inguinal hernia with graft or prosthesis, other and open repair of indirect inguinal hernia with graft or prosthesis, unilateral repair of inguinal hernia with graft or prosthesis, not otherwise specified, bilateral repair of inguinal hernia, not otherwise specified, other and open bilateral repair of direct inguinal hernia, other and open bilateral repair of indirect inguinal hernia, other and open bilateral repair of inguinal hernia, one direct and one indirect, other and open bilateral repair of direct inguinal hernia with graft or prosthesis, other and open bilateral repair of indirect inguinal hernia with graft or prosthesis, other and open bilateral repair of inguinal hernia, one direct and one indirect, with graft or prosthesis, bilateral inguinal hernia repair with graft or prosthesis, not otherwise specified, laparoscopic repair of umbilical hernia with graft or prosthesis, other laparoscopic umbilical herniorrhaphy, laparoscopic incisional hernia repair with graft or prosthesis.

The present invention can also be used in liver procedures, such as closed (percutaneous) (needle) biopsy of liver, open biopsy of liver, transjugular liver biopsy, laparoscopic liver biopsy, other diagnostic procedures on liver, marsupialization of lesion of liver, partial hepatectomy, open ablation of liver lesion or tissue, percutaneous ablation of liver lesion or tissue, laparoscopic ablation of liver lesion or tissue, other and unspecified ablation of liver lesion or tissue, other destruction of lesion of liver, auxiliary liver transplant, other transplant of liver, closure of laceration of liver, other repair of liver, percutaneous aspiration of liver, extracorporeal hepatic assistance, localized perfusion of liver, other injection of therapeutic substance into liver, and other operations on liver.

The present invention can also be used in pancreas procedures, such as closed (aspiration) (needle) (percutaneous) biopsy of pancreas, open biopsy of pancreas, other diagnostic procedures on pancreas, other excision or destruction of lesion or tissue of pancreas or pancreatic duct, proximal pancreatectomy, distal pancreatectomy, homotransplant of pancreas, heterotransplant of pancreas, autotransplantation of cells of islets of Langerhans, allotransplantation of cells of islets of Langerhans, other repair of pancreas, anastomosis of pancreas, other operations on pancreas.

The present invention can also be used in spleen procedures, such as excision of lesion or tissue of spleen, partial splenectomy, repair and plastic operations on spleen.

The present invention can also be used in stomach procedures, such as vagotomy not otherwise specified, truncal vagotomy, highly selective vagotomy, other selective vagotomy, transabdominal gastroscopy, gastroscopy through artificial stoma, other gastroscopy, closed [endoscopic] biopsy of stomach, open biopsy of stomach, other diagnostic procedures on stomach, dilation of pylorus by incision, endoscopic dilation of pylorus, other pyloroplasty, suture of gastric ulcer site, suture of duodenal ulcer site, endoscopic control of gastric or duodenal bleeding, transcatheter embolization for gastric or duodenal bleeding, other control of hemorrhage of stomach or duodenum, suture of laceration of stomach, closure of gastrostomy, closure of other gastric fistula, gastropexy, esophagogastroplasty, other procedures for creation of esophagogastric sphincteric competence, laparoscopic procedures for creation of esophagogastric sphincteric competence, ligation of gastric varices, intraoperative manipulation of stomach, insertion of gastric bubble (balloon), and laparoscopic gastric restrictive procedure.

The present invention can also be used in adhesiolysis procedures, such as common duct exploration for relief of other obstruction, incision of other bile ducts for relief of obstruction, laparoscopic lysis of peritoneal adhesions, other lysis of peritoneal adhesions, lysis of intraluminal adhesions of ureter, other lysis of perirenal or periureteral adhesions, laparoscopic lysis of perirenal or periureteral adhesions, laparoscopic lysis of adhesions of ovary and fallopian tube, other lysis of adhesions of ovary and fallopian tube, lysis of intraluminal adhesions of vagina, lysis of vulvar adhesions.

The present invention can also be used in bariatric procedures, such as other partial gastrectomy, high gastric bypass, laparoscopic gastroenterostomy, other gastroenterostomy, laparoscopic gastroplasty, laparoscopic gastric restrictive procedure, laparoscopic revision of gastric restrictive procedure, laparoscopic removal of gastric restrictive device(s), (Laparoscopic) adjustment of size of adjustable gastric restrictive device, and other operations on stomach.

The present invention can also be used in bowel reconstruction procedures, such as resection of small intestine for interposition, isolation of segment of large intestine, resegment for multiple lesions, other partial resection for small intestine, total removal of small intestine, partial excision of large intestine, multiple segmental resection of large intestine, segmental resection for multiple traumatic lessions of small intestine, cecectomy, resection of cecum of terminal ileum, right hemicolectomy; ileocolectomy; right radical colectomy, resection of transverse colon, left hemicolectomy, sigmoidectomy, other partial excision of large intestine; enterocolectomy NEC, laparoscopic total intra-abdominal colectomy, open total intra-abdominal colectomy, other and unspecified total intra-abdominal colectomy, intestinal anastomosis, not otherwise specified, small-to-small intestinal anastomosis, anastomosis of small intestine to rectal stump, other small-to-large intestinal anastomosis, large-to-large intestinal anastomosis, anastomosis to anus, incision of large intestine, transabdominal endoscopy of large intestine, endoscopy of large intestine through artificial stoma, colonoscopy, flexible sigmoidoscopy, closed endoscopic biopsy of large intestine, open biopsy of large intestine, other diagnostic procedures on large intestine, excision of lesion or tissue of large intestine, endoscopic polypectomy of large intestine, endoscopic destruction of other lesion or tissue of large intestine, other destruction of lesion of large intestine, open and other multiple segmental resection of large intestine, other and unspecified partial excision of large intestine, exteriorization of large intestine, resection of exteriorized segment of large intestine, other revision of stoma of large intestine, closure of stoma of large intestine, fixation of large intestine to abdominal wall, other fixation of large intestine, suture of laceration of large intestine, closure of fistula of large intestine, intra-abdominal manipulation of large intestine, dilation of intestine, revision of anastomosis of large intestine, local perfusion of large intestine, enterotomy, diagnostic procedures on other intestine, local excision or destruction of lesion or tissue of large intestine, isolation of intestinal segment, open and other partial excision of large intestine, total intra-abdominal colectomy, intestinal anastomosis, exteriorization of intestine, revision of intestinal stoma, closure of intestinal stoma, fixation of intestine, other repair of intestine, dilation and manipulation of intestine, other operations on intestines, proctostomy, diagnostic procedures on rectum, rectosigmoid, and perirectal tissue, transabdominal proctosigmoidoscopy, proctosigmoidoscopy through artificial stoma, rigid proctosigmoidoscopy, closed endoscopic biopsy of rectum, open biopsy of rectum, biopsy of perirectal tissue, other diagnostic procedures on rectum, rectosigmoid, and perirectal tissue, local excision or destruction of lesion or tissue of rectum, radical electrocoagulation of rectal lesion or tissue, other electrocoagulation of rectal lesion or tissue, destruction of rectal lesion or tissue by laser, destruction of rectal lesion or tissue by cryosurgery, local excision of rectal lesion or tissue, endoscopic polypectomy of rectum, pull-through resection of rectum, soave submucosal resection of rectum, laparoscopic pull-through resection of rectum, open pull-through resection of rectum, other pull-through resection of rectum, abdominoperineal resection of rectum, laparoscopic abdominoperineal resection of the rectum, open abdominoperineal resection of the rectum, other abdominoperineal resection of the rectum, other resection of rectum, transsacral rectosigmoidectomy, anterior resection of rectum with synchronous colostomy, other anterior resection of rectum, posterior resection of rectum, duhamel resection of rectum, repair of rectum, suture of laceration of rectum, closure of proctostomy, closure of other rectal fistula, rectorectostomy, abdominal proctopexy, other proctopexy, other repair of rectum, incision or excision of perirectal tissue or lesion, incision of perirectal tissue, excision of perirectal tissue, other operations on rectum and perirectal tissue, incision of rectal stricture, anorectal myectomy, repair of perirectal fistula, other operations on rectum and perirectal tissue.

The size and shape of a construct according to an embodiment of the present invention vary depending on the abdominal surgery the construct is to be used. For example, as shown in FIG. 1, a construct having a triangle shape with a dimension of 3 cm×3 cm×3 cm can be used in a liver resection where a tumor is removed from the liver. The construct is applied to cover the surgery site on the liver after the tumor removal. A rectangle shaped construct with a size of 3 cm×3-10 cm can also be used for a liver resection.

Figure 2:
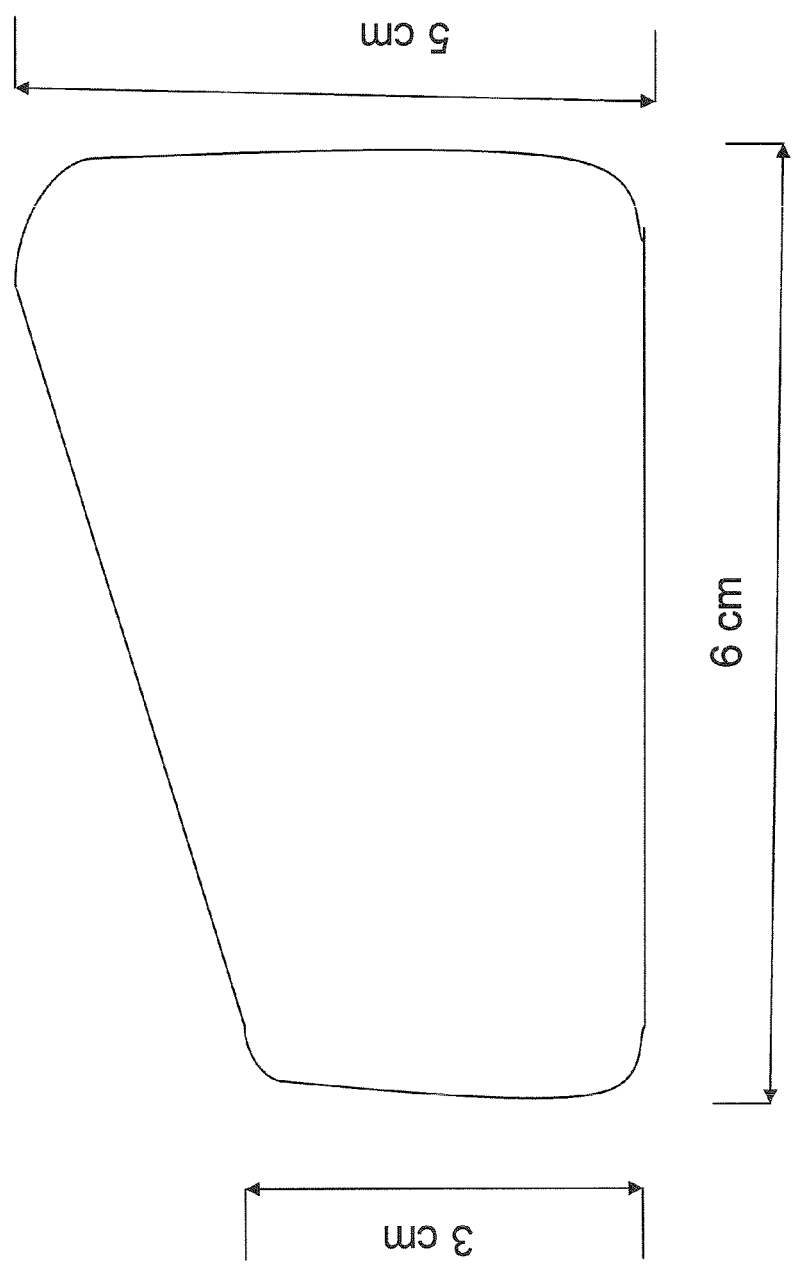
FIG. 2 illustrates a construct according to an embodiment of the present invention that can be used in a pancreatic surgery, the construct has round corners and a generally quadrilateral shape with the dimensions shown in the figure.
Figure 3:
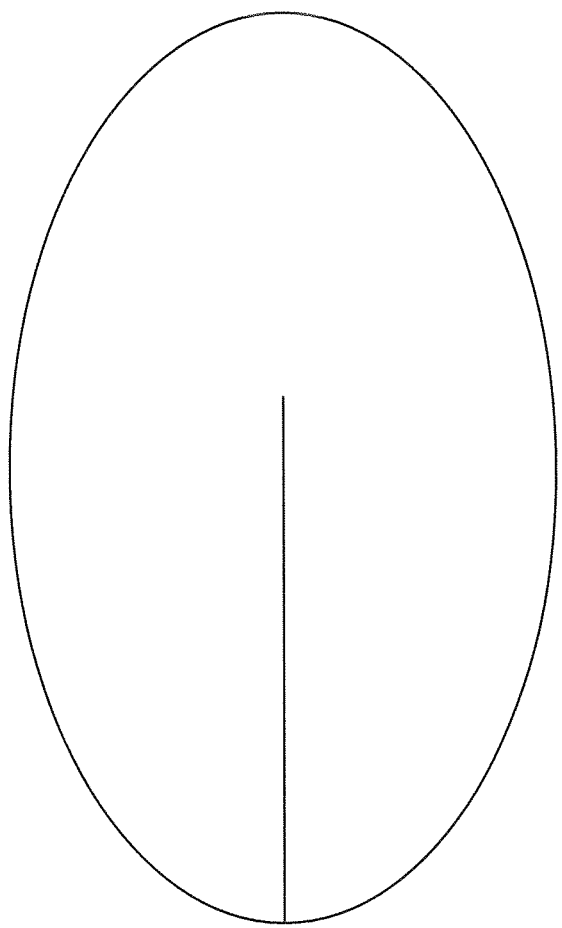
FIG. 3 illustrates a construct according to an embodiment of the present invention that can be used in a stomach surgery, the construct has round corners and a slit, it has a generally oval shape, with a dimension of 4-10 cm×6-12 cm.
Figure 4:
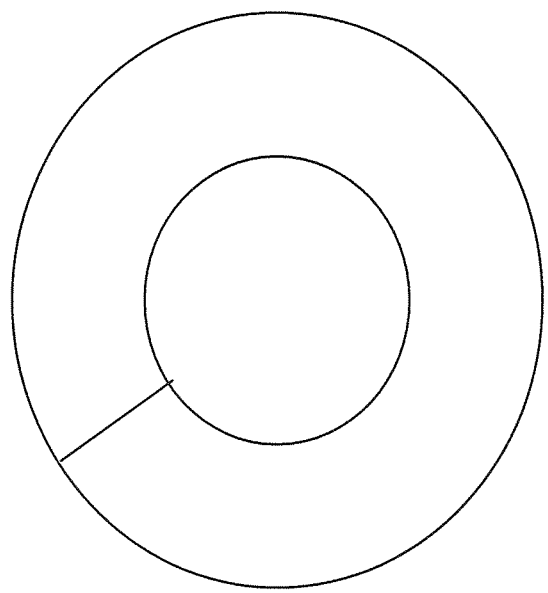
FIG. 4 illustrates a construct according to an embodiment of the present invention that can be used in a bariatric surgery, the construct has a donut shape and a slit.

FIGS. 2 to 4 illustrate constructs that can be used in a pancreatic surgery, a stomach surgery or a bariatric surgery. According to embodiments of the present invention, a construct having a quadrilateral shape can be used in pancreatic surgery, a construct having an oval shape can be used in stomach surgery, and a construct having a donut shape can be used in bariatric surgery.

As readily appreciated by those skilled in the art in view of the present disclosure, depending on the size and shape of the surgery site, such as the size of tumor to be removed, the construct to be used for in an abdominal surgery, such as a liver resection, may have a different size and shape.

According to embodiments of the present invention, the construct can optionally have one or more slits that allow easy application to the surgical site, or easy access of veins/vessels or other tissues at the application site. See, FIGS. 1, 3 and 4. The split can be made by various methods in view of the present disclosure, such as by cutting the construct at the desirable position while the construct is still wet.

In one embodiment of the present invention, the construct for use in an abdominal surgery can further comprise a frame, preferably a rigid or semi rigid frame for ease of application to the surgical site. The frame can be an implantable and resorbable frame, e.g., polymer mesh frame, or a disposable or a stainless steel frame.

In one embodiment of the present invention, one or more corners of the construct or allograft are rounded or flattened to prevent the corners from catching during implantation. In view of the present disclosure, any method known to those skilled in the art can be used to make the corners of the construct or allograft round or flatten.

In one embodiment of the present invention, the allograft in the construct can carry one or more therapeutic agents, such as growth enhancing agents, morphogenic proteins, small molecule compounds, pharmaceutical agents, anti-microbial agents, anti-inflammatory agent, agents that prevent scarring, adhesions and tethering of internal tissue at or near the surgery site, analgesics, etc., to further improve the performance and reduce the complications of abdominal surgeries. Examples of the growth enhancing agent include, but are not limited to, growth hormone, insulin like growth factor I, keratinocyte growth factor, fibroblast growth factor, epidermal growth factor, platelet derived growth factor and transforming growth factor, and a combination of any of the foregoing.

In another general aspect, embodiments of the present invention relate to a method of preparing a construct for use in an abdominal surgery. The construct can be made by drying an allograft of amnion and/or chorion membranes into the required shape over a frame, such as an implantable and resorbable frame, e.g., polymer mesh frame, or a disposable or stainless steel frame. Preferably, the frame is rigid or semi rigid. The frame can be any of the shapes suitable for the surgery, e.g., triangle, rectangle, quadrilateral, oval, donut, circle, semicircle, etc.

In an embodiment of the present invention, when a disposable frame is used, the dried tissue retains the shape of the frame when removed from the frame or could be packaged and sterilized with or without the disposable frame. The disposable frame can be removed and discarded prior to the use of the tissue. The disposable frame can be longer than the tissue for ease of handling and removal, or ease of application to the incision or surgical site.

In another embodiment of the present invention, an implantable and resorbable frame is used. Such frame could be a mesh or a solid frame with several holes throughout.

The allograft, such as that comprising one or more layers of human amnion and/or chorion tissues, is bonded to the frame by various methods in view of the present disclosure, such as, drying the tissue on the frame, using a resorbable adhesive, keeping the tissue wet and laying it on the frame, or freezing the tissue on the frame.

Another general aspect of the present invention relates to an improved method of performing an abdominal surgery. The improvement comprises covering an incision or a surgical site resulting from the surgery with a construct comprising an allograft comprising at least one layer of human amnion and chorion tissues, wherein the construct has a size and shape appropriate for covering the incision or the surgical site.

According to embodiments of the present invention, when an allograft comprises a combination of at least one layer of amnion and at least one layer of chorion tissues, the construct can cover an incision or surgical site with either the chorion tissue or the amnion tissue directly contacting the incision or surgical site.

Amnion tissue has two surfaces: (1) an outer surface in contact with chorion tissue; and (2) an inner surface in contact with amniotic fluid. Likewise, chorion tissue also has two surfaces: (1) an outer surface that is contact with maternal cells; and (2) and inner surface that is in contact with amnion tissue. According to embodiments of the present invention, either surface (ie. inner or outer) of either tissue of the allograft (ie. amnion or chorion) can be used to cover an incision or surgical site during a method of performing abdominal surgery of the present invention.

The improvement can be applied to any abdominal surgical procedure in view of the present disclosure. The circumference of the allograft can be larger than the incision or surgical site it will be implanted on so that when hydrated it will fully encase the surgical site. The circumference of the allograft can also be the same size as the incision or surgical site it will be implanted on.

In an embodiment of the present invention, a construct further comprising and implantable and resorbable frame is used to cover a surgical site resulting from an abdominal surgery.

In an embodiment of the present invention, a construct comprising at least one layer of amnion and chorion tissues is used to cover a skin incision resulting from an abdominal surgery. The allograft patch can be of any size suitable for covering the sutures or other type of tissue injuries at skin incision.

Preferably, a relatively thick layer of allograft is used to cover the skin incision. In one embodiment of the invention, the allograft patch has a thickness of about 2 mm to 4 mm. It can have multiple layers of amnion or a combination of multiple layers of amnion and chorion in any combination of amnion and chorion. The allograft can further comprise an implantable and resorbable frame that is applied to the skin incision along with the allograft.

In another embodiment of the present invention, amniotic fluid can be applied to the incision or surgical site to thereby cover the incision or surgical site with the amniotic fluid. The amniotic fluid can also be applied to cover a skin incision resulting from the surgery.

The amniotic fluid and the construct can be applied individually or in combination during the surgery. Preferably, the amniotic fluid is processed so that it has a relatively high viscosity for ease of application and for remaining in the desired area after the application. Methods known to those skilled in the art can be used to prepare amniotic fluid with a relatively high viscosity in view of the present disclosure.

In another embodiment of the present invention, a construct further comprising a frame is used to cover an incision or surgical site. The frame can be implantable and resorbable frame, such as a polymer mesh frame, or a disposable frame, such as a stainless steel frame.

The present invention overcomes shortcomings of the prior art by making human allograft membranes usable as surgical implants in an abdominal surgery.

There are several attributes which make an allograft having at least one of amnion and chorion tissues a preferred material for use in an abdominal surgery. Amnion has a complete lack of surface antigens, thus does not induce an immune response when implanted into a 'foreign' body, which is in contrast to most other allograft implants. Amnion also markedly suppresses the expression of the pro-inflammatory cytokines, IL-1α and IL-1β (Solomon et al., 2001, *Br J Ophthalmol.* 85(4):444-9) and produces natural inhibitors of matrix metalloproteases (MMPs) expressed by infiltrating polymorphonuclear cells and macrophages. Hao et al., 2000, *Cornea*, 19(3):348-52; Kim et al., 2000, *Exp Eye Res.* 70(3):329-37). Amnion also down-regulates TGF-β and its receptor expression by fibroblasts leading to the ability to modulate the healing of a wound by promoting tissue reconstruction. Furthermore, amnion and chorion contain antimicrobial compounds with broad spectrum activity against bacteria, fungi, protozoa, and viruses for reduced risk of post-operative infection. All of these characteristics of amnion make it a potential allograft candidate to be used in an abdominal surgery.

Human allograft amnion and chorion have the ability to prevent scarring, reduce inflammation, inhibit microbial infection and improve healing. The allografts have the ability to reduce adhesions, scar formation while also reducing inflammation and risk of post-operative infection.

Amnion, chorion and amniotic fluid used in the present invention can be prepared from birth tissue procured from a pregnant female. Informed consent is obtained from a pregnant female by following guidelines as promulgated by the American Association of Tissue Banks and consistent with guidelines provided the Food and Drug Administration: a federal agency in the Department of Health and Human Services established to regulate the release of new medical products and, finally, if required by an established review body of the participating hospitals or institutions. The pregnant female is informed that she will be subject to risk assessment to determine if she is qualified as a birth tissue donor. She will also be informed of the tests for the risk assessment. The pregnant female is further informed that, if she is selected as a birth tissue donor based on the risk assessment, her birth tissues, such as placenta and amniotic fluid, may be collected at birth, tested and processed for medical uses.

The informed consent includes consent for risk assessment and consent for donation of birth tissues.

Risk assessment is conducted on a pregnant female with informed consent to evaluate her risk factors for communicable diseases, such as human immunodeficiency virus (HIV), hepatitis B virus (HBV), hepatitis C virus (HCV), cytomegalovirus (CMV), human T-lymphotropic virus (HTLV), syphilis, etc. Medical and social histories of the pregnant female, including physical exam record, and/or risk assessment questionnaire, are reviewed. Pregnant females with high risk factors for the communicable diseases are excluded.

Consent to draw blood at time of delivery and 1 to 12 months post delivery is obtained from pregnant females with low risk factors for the communicable diseases. Screening tests on communicable diseases, such as HIV 1 and 2, HCV, HbCore, syphilis, HTLV I/II, CMV, hepatitis B and C, are conducted by conventional serological tests on the blood sample obtained at birth. The initial screening tests are preferably completed within 7 days after birth. Preferably, the screening tests are conducted again on a second blood sample collected a few months post delivery, to verify the previous screening results and to allow for detection of communicable disease acquired shortly before birth, but are shown as "negative" on the previous screening tests. The second blood sample can be collected 1-12 months, preferably 6 months, post birth.

Only pregnant females with informed consent who are tested negative for the communicable diseases are approved as birth tissue donors. In a preferred embodiment, only pregnant females with informed consent who are tested negative for the communicable diseases in both screening tests with the blood sample drawn at birth and the blood sample drawn 6 months post delivery are approved as birth tissue donors.

Sterile techniques and procedures should be used as much as practically possible in tissue handling, e.g., during tissue procurement, banking, transfer, etc., to prevent contamination of the collected tissues by exogenous pathogens.

Only birth tissues procured from the approved birth tissue donors are subject to the collection and subsequent processing. Birth tissues, such as placenta and amniotic fluid, are recovered from the delivery room and are transferred to a location in a sterile container, such as a sterile plastic bag or bottle. Preferably, the tissues are transferred in a thermally insulated device at a temperature of 4° to 28° C., for example, in an ice bucket.

According to an embodiment of the invention, shortly after its expulsion after birth, a suitable human placenta is placed in a sterile bag, which is placed in an ice bucket, and is delivered to another location. The placenta is rinsed, e.g., with sterile saline, to removed excessive blood clots. Preferably, the placenta is subject to aseptic processing, for example, by including one or more antibiotics, such as penicillin and/or streptomycin, in the rinse. The aseptically processed placenta is stored in a controlled environment, such as hypothermic conditions, to prevent or inhibit apoptosis and contamination.

The processed placenta is placed in a sterile container, such as one made of triple sterile plastic bags, packed in wet ice, and shipped to a location for subsequent processing via overnight courier. The placenta is shipped together with release documents for processing. For example, each shipment must include technical approval to process based upon a satisfactory review of the criteria for donor selection and donor approval. The shipment must also include results on screening of communicable diseases. Preferably, the shipment includes medical director review and approval of donor eligibility/suitability.

Upon receiving the shipment and a satisfactory review of the accompanying release documents, the amnion is separated from the chorion and other remaining tissues of placenta using methods known in the art in view of the present disclosure. For example, the amnion can be stripped off mechanically from the placenta immersed in an aseptic solution, e.g., by tweezers. The isolated amnion can be stored in a cryoprotective solution comprising a cryoprotective agent, such as dimethyl sulfoxide (DMSO) and glycerol, and cryopreserved by using a rapid, flash-freeze method or by controlled rate-freeze methods. Preferably, the isolated amnion is treated with one or more antibiotics, such as penicillin and/or streptomycin, prior to cryopreservation. The chorion can also be separated from the other tissues, preserved and stored for future use.

The isolated amnion is a tough, transparent, nerve-free and nonvascular sheet of membrane. It can be dried or lyophilized using various methods. For example, it can be dried over a sterile mesh, for example, by being placed on a sterile nitrocellulose filter paper and air dried for more than 50 minutes in a sterile environment. It can also be dried or lyophilized over other form of supporting material, which would facilitate the subsequent manipulation of the amnion, such as sterilizing, sizing, cataloging, and shipping of the amnion.

The present invention encompasses a kit comprising a construct for use in an abdominal surgery and instructions on how to use the construct in the abdominal surgery. Any of the constructs for use in an abdominal surgery according to embodiments of the present invention can be included in the kit. The construct comprises an allograft comprising at least one layer of human amnion and chorion tissues. The construct has a shape appropriate for covering an incision or a surgical site from an abdominal surgery. In a preferred embodiment, the kit comprises a plurality of constructs for abdominal surgery, and at least two of the plurality of constructs have different shapes or sizes suitable for covering different surgical sites. The allograft in the construct can further comprise one or more therapeutically active agents, such as anti-microbial agents, growth enhancing agents, anti-inflammatory agents, analgesics, etc.

According to an embodiment of the present application, the kit further comprises an amniotic fluid and instructions on how to use the amniotic fluid in the abdominal surgery. Preferably, the amniotic fluid is processed amniotic fluid having a relatively high viscosity.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. In a method of performing an abdominal surgery, the improvement comprising covering an incision or a surgical site resulting from the surgery with a construct comprising an allograft comprising at least one layer of human amnion tissue and optionally at least one layer of human chorion tissue, wherein the construct has one or more slits and a size and shape appropriate for covering the incision or the surgical site, wherein the abdominal surgery is selected from the group consisting of a liver surgery, a pancreatic surgery, a stomach surgery, a large intestinal surgery, and a small intestinal surgery.

2. In the method of claim 1, the construct further comprising an implantable and resorbable rigid or semi rigid frame.

3. In the method of claim 1, the improvement further comprising applying an amniotic fluid to the incision or the surgical site to thereby cover the incision or the surgical site with the amniotic fluid.

4. In the method of claim 1, the abdominal surgery being a liver resection, and the construct having a triangle or rectangle shape; the abdominal surgery being a pancreatic surgery and the construct having a quadrilateral; the abdominal surgery being a stomach surgery and the construct having an oval shape; or the abdominal surgery being a bariatric surgery and the construct having a donut shape.

5. In the method of claim 1, the construct comprising at least one layer of amnion tissue and at least one layer of chorion tissue, wherein in covering the surgical site with the construct, the at least one layer of chorion tissue is placed directly in contact with the surgical site.

6. In the method of claim 1, the improvement further comprising covering a skin incision resulting from the abdominal surgery with the construct.

7. In a method of performing an abdominal surgery, the improvement comprising covering an incision or a surgical site resulting from the surgery with a construct comprising an allograft comprising at least one layer of human amnion tissue and optionally at least one layer of human chorion tissue, wherein the construct has a size and shape appropriate for covering the incision or the surgical site, wherein the abdominal surgery is selected from the group consisting of a liver surgery, a pancreatic surgery, a stomach surgery, a large intestinal surgery, and a small intestinal surgery, and wherein the human amnion or chorion tissue of the allograft of the construct are obtained from birth tissue procured from a pregnant female donor, and the human amnion or chorion tissue is selected after conducting a screening test on the donor one to twelve months post-birth.

8. In a method of performing a bariatric surgery, the improvement comprising covering an incision or a surgical site resulting from the bariatric surgery with a construct comprising an allograft comprising at least one layer of human amnion tissue and optionally at least one layer of human chorion tissue, the construct having a donut shape and a slit.

9. In the method of claim 8, the construct comprising at least one layer of amnion tissue and at least one layer of chorion tissue, wherein in covering the surgical site with the construct, the at least one layer of chorion tissue is placed directly in contact with the surgical site.

10. In a method of performing a liver surgery, the improvement comprising covering an incision or a surgical site resulting from the liver surgery with a construct comprising an allograft comprising at least one layer of human amnion tissue and at least one layer of human chorion tissue, the construct having a triangle or rectangle size and shape and one or more slits, wherein in covering the surgical site with the construct, the at least one layer of chorion tissue is placed directly in contact with the surgical site.

11. In the method of claim 7, the construct further comprising an implantable and resorbable rigid or semi rigid frame.

12. In the method of claim 7, the improvement further comprising applying an amniotic fluid to the incision or the surgical site to thereby cover the incision or the surgical site with the amniotic fluid.

13. In the method of claim 7, the abdominal surgery being a liver resection, and the construct having a triangle or rectangle shape; the abdominal surgery being a pancreatic surgery and the construct having a quadrilateral; the abdominal surgery being a stomach surgery and the construct having an oval shape; or the abdominal surgery being a bariatric surgery and the construct having a donut shape.

14. In the method of claim 7, the construct comprising at least one layer of amnion tissue and at least one layer of chorion tissue, wherein in covering the surgical site with the construct, the at least one layer of chorion tissue is placed directly in contact with the surgical site.

15. In the method of claim 7, the improvement further comprising covering a skin incision resulting from the abdominal surgery with the construct.

* * * * *